US006597938B2

(12) United States Patent
Liu

(10) Patent No.: US 6,597,938 B2
(45) Date of Patent: Jul. 22, 2003

(54) SYSTEM FOR ASSISTANCE OF PARAMETER DETERMINATION AND DIAGNOSIS IN MRI DYNAMIC UPTAKE STUDIES

(75) Inventor: Kecheng Liu, Solon, OH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 09/932,551

(22) Filed: Aug. 16, 2001

(65) Prior Publication Data

US 2003/0036694 A1 Feb. 20, 2003

(51) Int. Cl.$^7$ .............................................. A61B 5/055
(52) U.S. Cl. ........................ 600/420; 600/431; 128/920
(58) Field of Search ................................ 600/407, 420, 600/431, 436; 128/920

(56) References Cited

U.S. PATENT DOCUMENTS

| | | | | |
|---|---|---|---|---|
| 4,477,923 | A | | 10/1984 | Baumann et al. ............. 378/95 |
| 5,377,681 | A | * | 1/1995 | Drane ......................... 600/419 |
| 5,417,213 | A | | 5/1995 | Prince ..................... 128/653.3 |
| 5,590,654 | A | | 1/1997 | Prince ..................... 128/653.4 |
| 5,713,358 | A | | 2/1998 | Mistretta et al. ............ 600/420 |
| 5,746,208 | A | | 5/1998 | Prince ......................... 600/420 |
| 5,840,026 | A | * | 11/1998 | Uber et al. .................. 600/431 |
| 5,896,439 | A | | 4/1999 | Krause et al. ................ 378/95 |
| 5,924,987 | A | * | 7/1999 | Meaney et al. ............. 600/420 |
| 6,032,678 | A | * | 3/2000 | Rottem ....................... 600/437 |
| 6,073,042 | A | | 6/2000 | Simonetti ................... 600/420 |
| 6,195,579 | B1 | | 2/2001 | Carroll et al. .............. 600/420 |
| 6,233,475 | B1 | | 5/2001 | Kim et al. ................... 600/420 |
| 6,337,992 | B1 | * | 1/2002 | Gelman ....................... 600/425 |

OTHER PUBLICATIONS

Dimitroula et al., FUNAGES: An Expert System for Fundus Fluorescein Angiography, Proc. 6th Int. Symposium on Health Information Management Research, May 2001, pp75–79.*

Hoe, et al. "Determination of Scan Delay time in Spiral CT–Angiography: Utility of a Test Bolus Injection." *Journal of Computer Assisted Tomography*, © Mar./Apr. 1995 Raven Press, New York NY. pp. 216–220.

Earls, et al. "Hepatic Arterial–Phase Dynamic Gadolinium–enhanced MR Imaging: Optimization with a Test Examination and a Power Injector." © RSNA 1997.

Prince, et al. "Contrast–enhanced Abdominal MR Angiography: Optimization of Imaging Delay Time by Automating the Detection of Contrast Material Arrival in the Aorta." © RSNA 1997.

(List continued on next page.)

*Primary Examiner*—Marvin M. Lateef
*Assistant Examiner*—Barry Pass
(74) *Attorney, Agent, or Firm*—Fay, Sharpe, Fagan, Minnich & McKee, LLP

(57) ABSTRACT

A parameter compilation memory (62, 114) stores patient physiological information and contrast agent arrival or uptake times ($t_D$, $t_A$, $t_V$) from past patients. A triggering or synchronizing window processor (64, 112) sets a triggering window, i.e. estimates the arrival time, based on the past patient information. A subject (16) disposed within an imaging region (12, 90) is injected with a contrast agent (66). Arrival of the contrast agent in the imaging region is detected (72, 110) with a real time tracking method. Diagnostic imaging is commenced on the first to occur of the detection of contrast agent arrival within the window and the end of the triggering window. The uptake times for the subject (16) are compared to those stored in the memory (62, 114) and analyzed to propose a diagnosis.

18 Claims, 3 Drawing Sheets

OTHER PUBLICATIONS

Foo, et al. "Single Bolus Contrast Enhanced Peripheral #D MRA using Automated Table Motion Integrated with Automated Bolus Detection and Acquisition Triggering."

Wilman, et al. "Fluoroscopically Triggered Contrast-enhanced Three-dimensional MR Angiography with Elliptical Centric View order: Application to the Renal Arteries." © RSNA 1997.

Korosec, et al. "Time-Resolved Contrast-Enhanced 3D MR Angiography." © 1996 Williams & Wilkins.

Wang, et al. Contrast enhanced MRA of the lower extremity: arterial-venous transit of contrast bolus and venous contamination. © 2001 Proc. Intnl. Soc. Mag. Reson. Med 9.

Marcos, et al. "Automated Real-time Multi-station Projection MR Angiography ('Bolus Prep')." © 2001, Proc. Intl. Soc. Mag. Reson. Med 9.

* cited by examiner

SYSTEM FOR ASSISTANCE OF PARAMETER DETERMINATION AND DIAGNOSIS IN MRI DYNAMIC UPTAKE STUDIES

BACKGROUND OF THE INVENTION

The present invention relates to the diagnostic imaging arts. It finds particular application in conjunction with contrast agent enhanced angiography such as magnetic resonance and computed tomography angiography and will be described with particular reference thereto. It will be appreciated, however, that the invention is also applicable to other types of magnetic resonance flow imaging and contrast agent enhanced imaging in other modalities.

Magnetic resonance angiography is used to view the blood vessels of the body. Dipoles in the blood of the subject are excited and imaged as they propagate through vessels of interest. A clinician analyzes the images to identify various circulatory abnormalities, such as slow flow points, partial blockages within vessels in the image, complete occlusions, and the like.

In magnetic resonance angiography, the dipoles being imaged are in motion. Advantageously, the dipoles move though an imaging region, traveling along in the bloodstream. Magnetic resonance angiography imaging can be enhanced with a contrast agent, which is injected into the blood. A sequence is selected that shows the contrast agent very well against other tissue in a magnetic resonance image. Thus, it is very useful for viewing the blood vessels of the body.

Most often, the contrast agent is injected into a region of the subject outside the imaged region. The injected contrast agent, or bolus, travels in the bloodstream for a period of time before it reaches the imaging region. Timing the arrival of the bolus is critical in that there is a small time window in which the contrast agent is at its peak concentration in the examination region, i.e. when the optimum image can be acquired. Multiple factors play a role in the travel time of the bolus, such as position of the region of interest relative to the injection of the contrast agent, subject age, sex, and weight, and vascular anomalies such as obstructions in blood vessels.

Prior methods for estimating the arrival time of the bolus do not adequately predict arrival times for all patients. In a test bolus method, a small amount of contrast agent, that is, a test bolus, is injected into the patient. The region of interest is monitored by taking real-time fluoroscopic images at a rate of about one per second of the region of interest. The time that the test bolus takes to show up in the fluoroscopic images is recorded. A second injection, this time with the full bolus, is administered to the subject. The operator waits the amount of time it took the test bolus to reach the region of interest before initiating a diagnostic scan.

Although simple and straightforward, the test bolus method has drawbacks. In practice, 20–25% of trials run using this method fail to detect the test bolus. If the test bolus is not detected, the operator typically makes a subjective guess based on his/her experience. Additionally, the test bolus method requires an extra injection of contrast agent. This adds to patient discomfort, and the test bolus is partially absorbed as it travels through the region of interest, degrading contrast and definition in the final image. Moreover, the fluoroscopy monitoring for the test bolus has a low temporal resolution, about one frame per second which limits the accuracy of the predicted delay time. Further, the timing parameters of the test bolus may not be the same due to significantly different intravascular bolus concentrations. Patient movement between or during scans can also affect how the test bolus and the real bolus move through the subject.

Other methods include real time tracking of a single, large bolus. One full strength injection is given to the patient, and the examination is monitored for the arrival of the contrast agent. One method of tracking the bolus involves repeatedly monitoring a single line of k-space for magnetic resonance signal intensity changes. In k-space, the intensity of the signal spikes when the region of interest receives the bolus. Problems with this method include a lack of a base image, and sensitivity to physical motion. Because the tracking signal does not generate images, the operator cannot see the traveling bolus and must rely solely on the machine or intuition to make the decision to start imaging. Movement can also affect this method. Slight movement during the scan can falsely trigger a diagnostic image. For example, moving fat dipoles into the monitored region of interest causes the signal intensity to rise.

Real time fluoroscopic images can be used without the a bolus. In this method, the operator watches the fluoroscopic images, when he/she thinks the bolus has arrived, the diagnostic image data acquisition is initiated by the operator. Drawbacks to this method include its low temporal resolution and subjective triggering. Typically, temporal resolution is on the order of one frame per second. However, temporal resolution can be reduced at the expense of image quality.

Another method is the TRICKS method which samples the center of k-space more frequently than other portions of k-space. Resultantly, the probability of catching the plateau period of the signal increases. However, undersampling of the non-central portions of k-space means loss of high and middle frequency information. This method can be thought of as a "blind" oversampling of center k-space, as it is not guaranteed to catch the plateau period, and can miss the bolus entirely.

The present invention provides a new and improved method and apparatus which overcomes the above-referenced problems and others.

SUMMARY OF THE INVENTION

In accordance with one aspect of the present invention, a method of angiographic imaging is provided. A region of interest of a subject is disposed in an examination region. Physical parameters of the subject are entered into a parameter database. Triggering information is calculated from previously entered information to the parameter database. A contrast agent is injected into the patient and monitoring for the arrival of the contrast agent to a region of interest is commenced. A diagnostic imaging scan is initiated in response to the arrival of the contrast agent and the parameter database is updated.

In accordance with another aspect of the present invention, a method of diagnosing vascular anomalies is provided. A subject is injected with a contrast agent. Angiographic images are generated of a region of interest of the subject. Times $t_D$, $t_A$, and $t_V$ are measured and compared to a database that includes recorded times $t_D$, $t_A$, and $t_V$ of a multiplicity of patients.

In accordance with another aspect of the present invention, a diagnostic imaging apparatus is provided. A parameter compilation memory stores contrast agent uptake times from a plurality of prior scans of other subjects. A contrast agent detection circuit verifies successful detection of the agent and loads the uptake times into the parameter compilation memory. A reconstruction processor reconstructs received data signals into an image representation of the subject.

In accordance with another aspect of the present invention, a diagnostic imaging apparatus is provided. The apparatus includes a means for generating contrast agent enhanced diagnostic images, a parameter memory, a means for determining the contrast agent related parameters, a means for comparing the parameters, and a means for analyzing the parameters.

In accordance with another aspect of the present invention, an angiographic imaging apparatus is provided. The apparatus includes a means for generating contrast agent enhanced diagnostic images, a means for monitoring contrast agent arrivals, a memory means that stores arrival time of past patients and past patient physiological characteristics, and a means for determining a projected arrival window.

One advantage of the present invention resides in more robust bolus detection.

Another advantage resides in an accumulation of knowledge and the use of the knowledge to improve future scans.

Another advantage resides in the ability to search for vascular anomalies prior to generating a magnetic resonance angiography image.

Another advantage resides in the ability to perform a clinical diagnosis based on detected imaging parameters related withe physiological conditions or changes in a patient.

Still further benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENT

Figure 1:
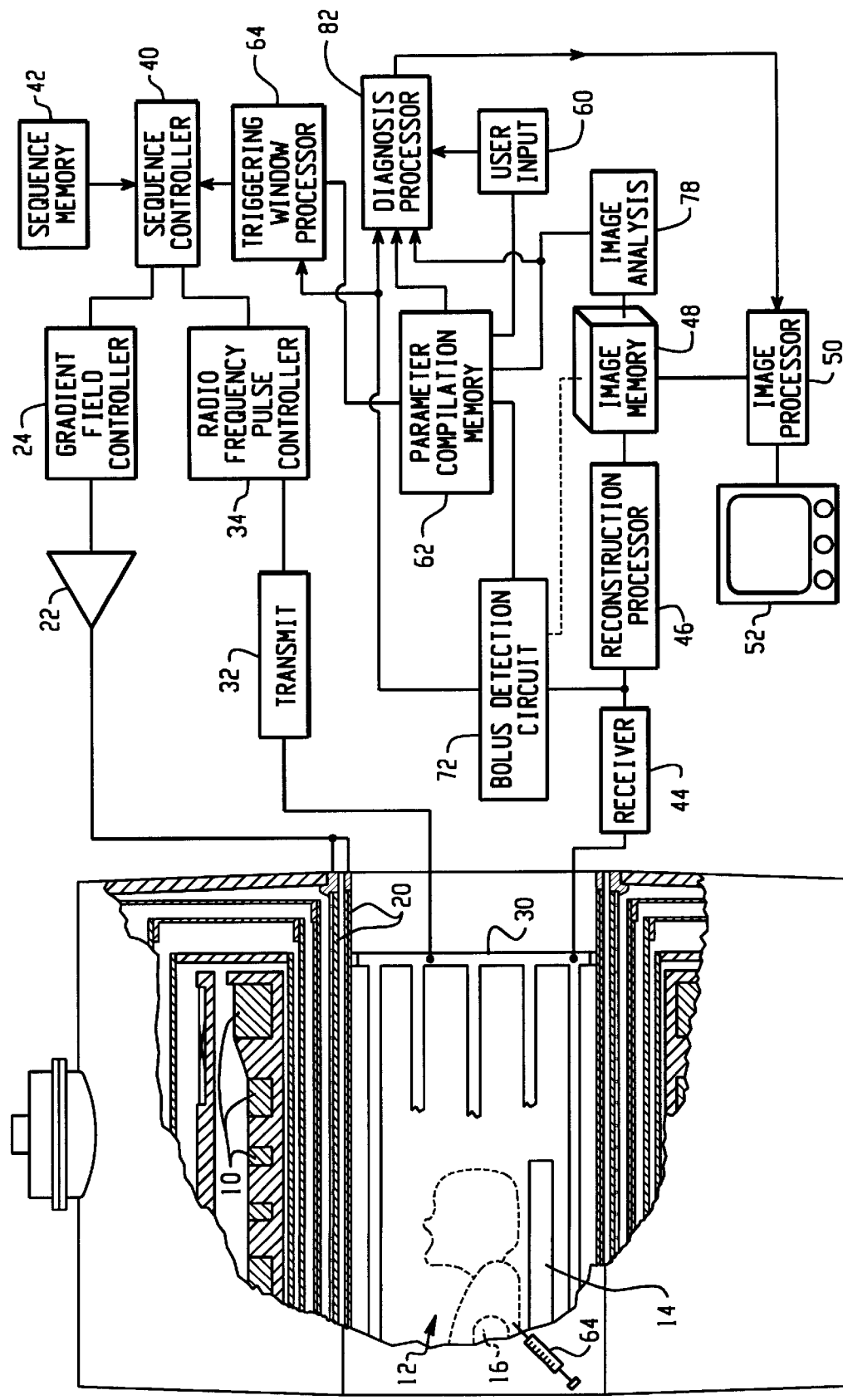
FIG. 1 is a diagrammatic illustration of a magnetic resonance apparatus for performing magnetic resonance angiography scans in accordance with the present invention.

With reference to FIG. 1, a magnetic resonance diagnostic imaging apparatus generates a volumetric image of an internal region of the patient including a blood vessel such as the aorta or the carotid artery. The diagnostic imager, in the illustrated embodiment, is a horizontal field magnetic resonance imaging system that includes a solenoidal, preferably superconducting, magnet 10. It is to be understood that an open, vertical field magnet assembly is also applicable. The horizontal field arrangement typically offers higher fields and steeper gradient fields. However, an open system offers improved patient access and possible application in interventional surgery and other applications. The magnet 10 generates a horizontal magnetic field through an imaging region 12 along the axis of its bore. A patient support 14 is movable in and out of the bore to position a region of interest of a subject 16 in the imaging region 12 at the isocenter or the bore. For imaging, at least one gradient coil assembly 20 superimposes gradient magnetic fields upon the main magnetic field for spatially encoding the main magnetic field. The gradient assembly 20 is attached to a gradient amplifier 22. The amplifier 22 amplifies pulse signals from a gradient field pulse controller 24.

A whole body RF coil 30 receives RF pulses from an RF pulse transmitter 32, preferably a digital transmitter, for transmission into the imaging region 12. The RF transmitter 32 receives the RF pulse information from an RF pulse controller 34. A sequence controller 40 withdraws a selected sequence from a sequence memory 42 and coordinates the gradient field controller 24 and the RF pulse controller 34 such that they produce a combination of pulses that reflects the selected sequence. In contrast enhanced imaging, the sequence controller also causes initiation of the imaging sequence.

Upon transmission into the imaging region 12 the RF pulses excite and manipulate dipoles selected by the gradient pulses. Magnetic resonance signals are detected by the whole body RF coil 30, or other local receive coils and received and demodulated by at least one receiver 44, preferably digital. The received magnetic resonance signals are reconstructed by a reconstruction processor 46 by applying a Fourier transform or other appropriate reconstruction algorithm, then stored in a volumetric image memory 48. An image processor 50 withdraws selected portions of the reconstructed image and formats them for display on a human readable display 52, such as a computer monitor, active matrix monitor, liquid crystal display, and the like.

In the preferred embodiment the magnetic resonance apparatus described previously is used to perform magnetic resonance angiography scans on the subject 16. Prior to the initiation of the scan, an operator enters known factors about the subject 16 at a user input terminal 60, such as age, sex, weight, region to be imaged, venous or arterial images, and the like. Other factors that the operator enters at this point are any known vascular abnormalities, such as high or low blood pressure, cholesterol level, and known occlusions or blockages. Based upon the entered factors, the apparatus consults a parameter compilation memory 62 and retrieves a temporal triggering window. The parameter compilation memory 62 includes data from a multiplicity of prior scans, each scan experiencing the successful detection of a contrast bolus. The memory 62 compares the input data about the subject with stored data from past scans on other similar patients. From the successful past scans, combined with statistical probabilities and uncertainties, a triggering window processor 64 determines a window of time in which the contrast bolus is expected to arrive in the imaging region of the present subject.

A bolus of contrast agent 66 is injected into the subject 16. In the preferred embodiment, a real time bolus tracking method is initiated concurrently. The real time tracking method includes at least one of the methods discussed in the background section, such as fluoroscopic images or central k-space signal tracking. Optionally, a real time tracking method not discussed herein is used.

Figure 2:
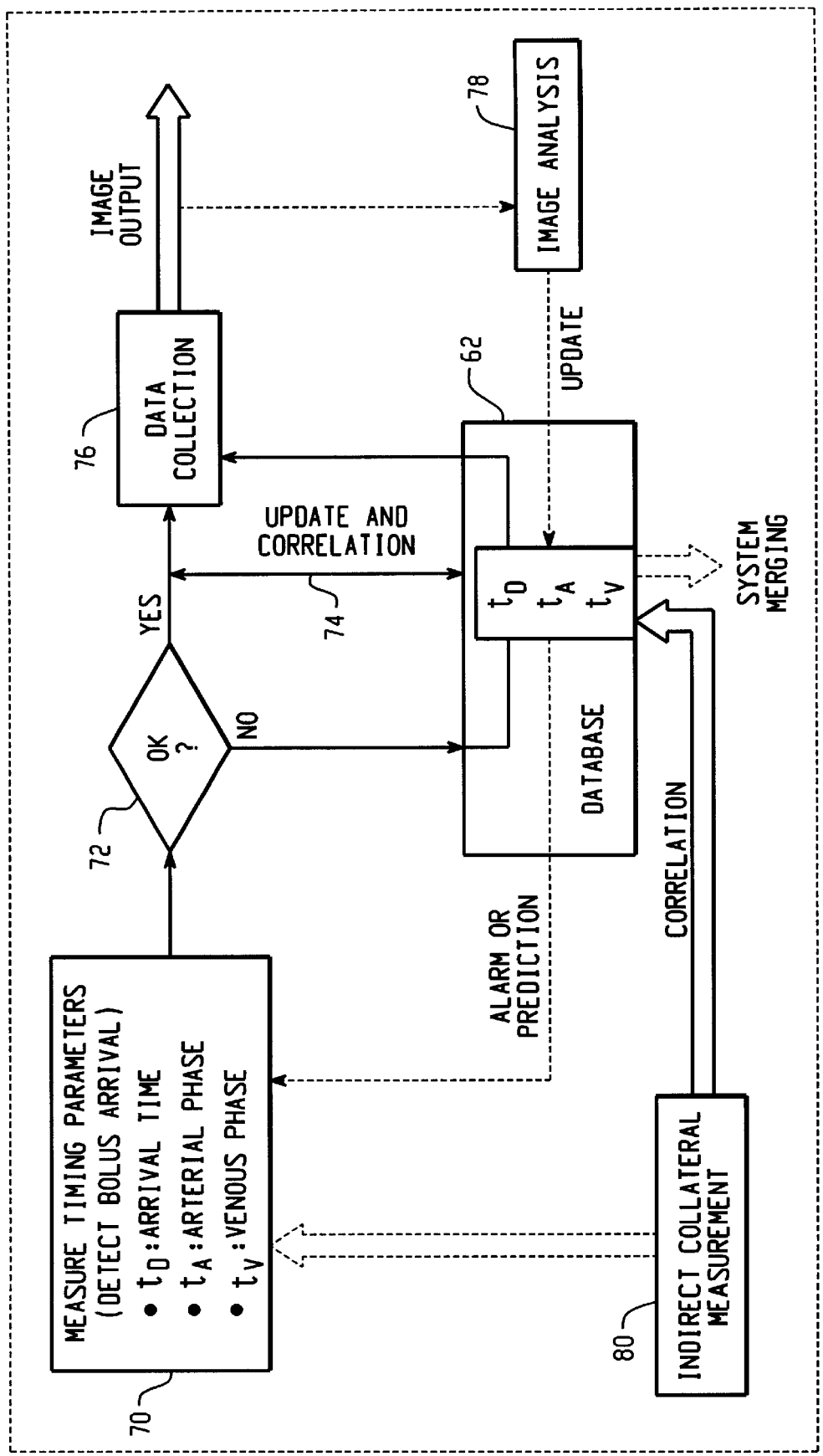
FIG. 2 is a flow diagram illustrating an image production and memory updating process, in accordance with the present invention.

With reference to FIG. 2, and with continuing reference to FIG. 1, the magnetic resonance apparatus detects 70 the arrival of the bolus in the region of interest 12 with a bolus detection circuit 71. The detection circuit 71 monitors the receiver output in the central k-space tracking technique. In the fluoroscopic detection technique, the reconstruction processor generates fluoroscopic images which the detection circuit 71 analyzes. Other detection circuit configurations and placements are contemplated as are appropriate to the detection technique. A verification step 72 verifies a detection of the bolus. If the verification circuit 72 determines that detection of the bolus 66 has successfully occurred, the triggering window processor 64 is notified and the parameter compilation memory 62 is updated 74. The entered parameters of the subject (e.g. weight, age, etc.) are stored along with critical waypoints in the bolus travel time. A time $t_D$ is recorded that indicates the arrival (detection time) of the bolus in the region of interest. Where appropriate, a time $t_A$ is recorded that indicates the contrast agent concentration peak in arteries in the region of interest, that is, the arterial phase. A time $t_V$ is recorded that indicates the peak contrast agent concentration in the veins in the region of interest, that is, the optimal venous imaging phase.

The critical times $t_D$, $t_A$, and $t_V$ are added to the parameter compilation memory 62 along with the entered parameters of the subject 16 and the system becomes "smarter". With each successful scan, the system gains more information with which to predict bolus travel times of future scans.

If bolus detection is triggered before the triggering window starts, initiation of imaging is blocked and the monitoring for bolus arrival is continued. In the preferred embodiment, the system provides the operator with an alarm or signal when the triggering window starts. At any time within the triggering window, the operator may manually initiate the diagnostic scan. In the event that the bolus is not detected, and the operator does not manually initiate the scan, the triggering window processor automatically initiates the imaging sequence at the end of the triggering window.

Regardless of triggering method, a magnetic resonance angiography imaging scan is performed during a data collection step 76 and an image is reconstructed by the reconstruction processor 46. Some real time bolus tracking methods do not acquire all of the values $t_D$, $t_A$, and $t_V$. For example, k-space intensity monitoring only provides the time $t_D$. In a case where all of the critical times are not acquired prior to the diagnostic scan, post-patient analysis is performed on the reconstructed image data by an image analyzer 78 to determine the other times and, optionally, other information such as occlusion locations and the like.

In addition to its own successful scans, the system also "learns" by linking with other systems. In the preferred embodiment, the system accesses a parameter compilation memory of a similar system, downloads information, and integrates it into its own parameter compilation memory. In the preferred embodiment, similar systems are networked, and routine integrations are performed, for instance, on a nightly basis. Alternately, two or more systems share and update a common memory. Alternately, a CD or other similar storage device is used to transfer compiled information to another system. It is also contemplated that non-analogous systems be linked. For instance, similar bolus tracking experiments are performed on a CT scanner. A memory database from the CT scanner including the critical uptake times is transferred and integrated into the MR system of the preferred embodiment. This is possible because the circulation of the contrast agent is dependent on patient physiological conditions rather than the specific imaging modality.

As an additional guide to obtaining an accurate timing window in an MRI scan, a collateral pilot scan 80 is run without any contrast agent. In the pilot scan, a sequence is selected that highlights possible occlusions or anomalies in the proposed region of interest for the diagnostic scan. The image processor 78 or the operator identifies any such anomalies for inclusion with the subject profile entered in the database of the parameter compilation memory. For example, a pilot scan detects a partial blockage of the aorta in a 35 year old, 210 lb. male patient. This data is cataloged differently than data from a similar male patient with no blockages. In short, the more information about the health of the patient the system has before the scan, the more apt it is to predict accurate bolus travel times.

In accordance with another aspect of the present invention, a diagnosis processor 82 compares the critical times obtained from the subject with the historical data in the parameter compilation memory and generates a display of proposed diagnoses. A diagnostic scan is performed as described above, and the measured critical times $t_D$, $t_A$, and $t_V$ are compared to those of past patients with similar patient profiles. If the values $t_D$, $t_A$, and $t_V$ of the present patient vary greatly from the medians of similar patients, otherwise similar patients with like variations from the medians are identified and their diagnoses are retrieved. For instance, if the three times $t_D$, $t_A$, and $t_V$ occur much later than expected, it suggests a partial blockage upstream of the region of interest. If $t_D$ and $t_A$ are normal and $t_V$ is delayed, a block in the veins is suggested, and so forth.

Figure 3:
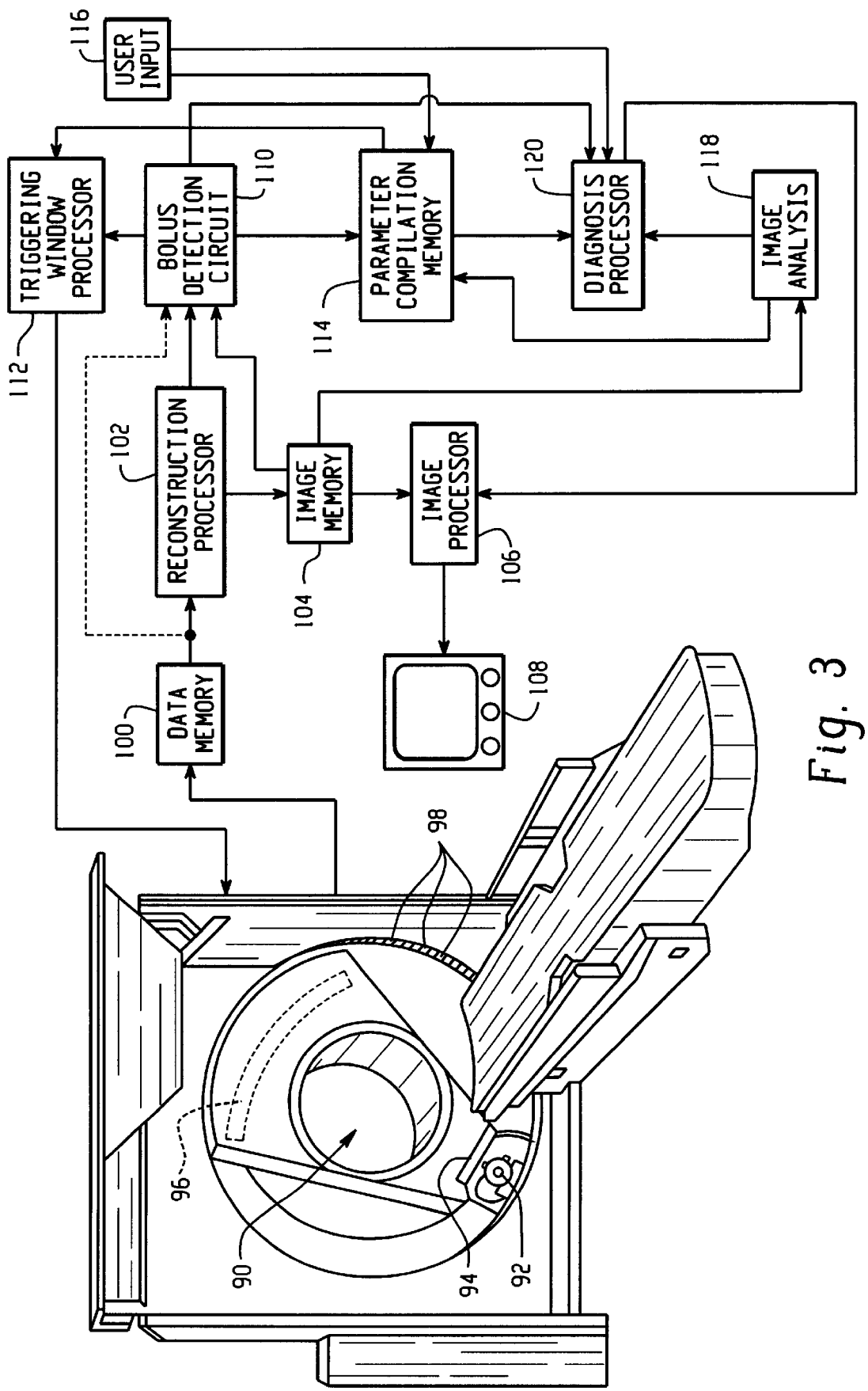
FIG. 3 is a diagrammatic illustration of a computer tomography (CT) embodiment for performing angiography scans, an accordance with the present invention.

In another preferred embodiment, and with reference to FIG. 3, a computed tomography scanner is used to perform a dynamic uptake study. The subject is disposed in an imaging region 90 of the scanner. In a third and fourth generation scanners, x-rays generated at a source 92 are focused into a fan beam by a collimator 94 and pass through the imaging region. In a third generation (rotate-rotate) scanner, a detector array 96 detects x-rays that have passed through the imaging region 90. In a fourth generation (rotate-stationary) scanner, individual detectors 98 line an outer gantry, detecting x-rays while the fan beam is pointed at them. Data lines or sets from the detected x-rays are collected into a data memory 100 from which they are reconstructed. A reconstruction processor 102 reconstructs the data sets into an image representation which is stored in an image memory 104. An image processor 106 withdraws selected portions of the image representation and formats them for viewing on a human readable display 108.

In the preferred CT embodiment, a contrast agent is injected into the subject and a fluoroscopic scan mode is initiated. Lower resolution fluoroscopic CT images are reconstructed and stored in the image memory 104. Preferably, the reconstruction processor does not reconstruct a full new image with each rotation of the fan beam. Preferably, the reconstruction processor reconstructs the most recently collected 180° plus the fan angle of data sets. In this manner, the image is updated as each data set is collected for substantially real time imaging. A contrast agent bolus detection circuit 110 monitors a selected region of the reconstructed image for a change indicative of the contrast agent's arrival. Because CT contrast agents typically enhance the contrast of the blood vessels, the region typically lightens. Alternately, the detection circuit 110 monitors selected portions of each data set for lightening. Once the region of interest is selected, the portion of the fan beam at each sampling angle that intersects the selected anatomical region is readily calculated, which portion is monitored for changes indicative of the arrival of the contrast agent.

A triggering window processor 112 changes the scanning mode from fluoroscopic to a selected imaging mode, such as a high resolution radiographic spiral imaging mode based on the signal from the detection circuit or the default parameters from a historical data compilation memory 114 as discussed above. Preferably, the historical memory is updated by user input 116 or an image analysis processor 118 as discussed above. A diagnosis processor 120 compares the scan results with the historical scan results and retrieves the corresponding diagnoses as discussed above.

It is to be appreciated that the described method and apparatus are applicable to other imaging modalities, such as digital x-ray, dual isotope SPECT or PET imaging, and the like.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A method of angiographic imaging comprising:
   disposing a region of interest of a subject in an examination region;
   entering physical parameters of the subject into a parameter database;
   accessing the parameter database to determine diagnostic imaging triggering information for the from a projected contrast arrival window subject;
   injecting a contrast agent into the subject;
   monitoring for an arrival of the contrast agent in a region of interest;
   initiating an angiographic imaging scan in response to detecting the arrival of the contrast agent and the determined triggering information; and, updating the parameter database.

2. The method as set forth in claim 1, wherein the parameters include:
   an age of the subject;
   a sex of the subject;
   a weight of the subject; and,
   vascular abnormalities of the subject.

3. The method as set forth in claim 1, wherein the step of monitoring for the arrival of the contrast agent includes at least one of:
   fluoroscopic image tracking;
   k-space signal tracking;
   repetitive sampling of select central k-space values; and,
   repetitive sampling of portions of collected data sets.

4. The method as set forth in claim 1, further including:
   generating a pilot image sensitive to blood flow velocities in the region of interest of the subject;
   diagnosing occlusions of blood vessels in the region of interest.

5. A method of angiographic imaging comprising:
   disposing a region of interest of a subject in an examination region;
   entering physical parameters of the subject into a prior subject database which correlates the physical parameters to normal contrast agent arrival times of prior subjects to determine a normal contrast agent arrival time window for the subject;
   injecting a contrast agent into the subject;
   monitoring for an arrival of the contrast agent in a region of interest;
   initiating an angiographic imaging scan in response to detecting the arrival of the contrast agent within the determined contrast agent arrival time window;
   analyzing the angiographic images to determine refined physical parameters of the subject for updating the parameter database; and,
   updating the prior subject database with the refined physical parameter and a time at which the contrast agent was monitored as arriving in the region of interest.

6. A method of angiographic imaging including:
   determining a temporal triggering window within which window the initiating of an angiographic imaging scan is permitted by entering physical parameters of a present subject into a parameter database and retrieving a triggering window based on contrast agent arrival times at a region of interest information of past subjects with similar physical parameters;
   injecting a contrast agent into the subject;
   monitoring for the arrival of the contrast agent at the region of interest of the subject;
   initiating a diagnostic scan based on the arrival of the contrast agent and the determined temporal triggering window; and,
   updating the parameter database with the monitored contrast agent arrival time and the entered physical parameters.

7. The method as set forth in claim 6, further including:
   in the absence of detecting the arrival of the contrast agent in the region of interest, initiating the imaging scan at the end of the triggering window.

8. A method of angiographic imaging comprising:
   disposing a region of interest of a subject in an examination region;
   conducting a collateral angiography scan to detect physiological conditions that affect a projected arrival time of the contrast agent;
   entering the detected physiological conditions and other physical parameters into a parameter database and retrieving a corresponding temporal triggering window in which the contrast agent is expected to arrive in the region of interest;
   injecting a contrast agent into the subject;
   monitoring for an arrival of the contrast agent in a region of interest;
   initiating an angiographic imaging scan in response to detecting the arrival of the contrast agent within the retrieved temporal triggering window; and,
   updating the parameter database.

9. A method of angiographic imaging comprising:
   disposing a region of interest of a subject in an examination region;
   entering physical parameters of the subject into a parameter database and deriving diagnostic imaging triggering information for the subject;
   injecting a contrast agent into the subject;
   monitoring for an arrival of the contrast agent in a region of interest and determining values of a contrast agent arrival time $t_D$, an arterial phase contrast agent time $t_A$ and a venous phase contrast agent time $t_V$ of the subject;
   comparing the determined arrival times $t_D$, $t_A$ and $t_V$ against values stored in the parameter database;
   initiating an angiographic imaging scan in response to detecting the arrival of the contrast agent and the determined triggering information; and,
   making a proposed diagnosis of the subject based on the determined arrival times $t_D$, $t_A$ and $t_V$ of the subject and the stored values from the parameter database.

10. A method of angiographic imaging comprising:
   disposing a region of interest of a subject in an examination region;
   entering physical parameters of the subject into a parameter database;
   accessing the parameter database to determine diagnostic imaging triggering information for the from a projected contrast arrival window subject;
   performing a pilot imaging scan sensitive to blood flow velocities in the region of interest of the subject;
   injecting a contrast agent into the subject;
   monitoring for an arrival of the contrast agent in a region of interest;
   initiating a dynamic uptake angiographic imaging scan in response to detecting the arrival of the contrast agent and the determined triggering information; and,
   diagnosing occlusions of blood vessels in the region of interest from the dynamic uptake magnetic resonance angiography imaging scan and the pilot imaging scan downstream of the injected contrast agent; and,
   updating the parameter database with monitored contrast agent and diagnosed occlusion information.

11. A method of diagnosing vascular anomalies comprising:
   injecting a subject with a contrast agent;
   accessing a database which correlates physical parameters and contrast agent arrival times of past subjects to retrieve a projected contrast agent arrival window within which angiographic imaging of the subject is permitted;
   within the retrieved contrast arrival window, generating angiographic images of a region of interest of the subject;
   measuring a contrast agent arrival time $t_D$ in the region of interest;
   measuring an arterial phase time $t_A$ in which the contrast agent enhances arterial blood flow;
   measuring a venous phase time $t_V$ in which the contrast agent enhances venous blood flow;
   comparing the measured times $t_D$, $t_A$, and $t_V$ to a database containing values of $t_D$, $t_A$, and $t_V$ of a multiplicity of patients.

12. A method of diagnosing vascular anomalies comprising:
   injecting a subject with a contrast agent;
   generating angiographic images of a region of interest of the subject;
   measuring a contrast agent arrival time $t_D$ in the region of interest;
   measuring an arterial phase time $t_A$ in which the contrast agent enhances arterial blood flow;
   measuring a venous phase time $t_V$ in which the contrast agent enhances venous blood flow;
   comparing the measured times $t_D$, $t_A$, and $t_V$ to a database that includes patient physiological information and diagnoses, including values of $t_D$, $t_A$, and $t_V$ of a multiplicity of patients;
   displaying the diagnoses from the database of patients with similar physiological information and values of $t_D$, $t_A$, and $t_V$.

13. A diagnostic imaging apparatus comprising:
   a parameter compilation memory in which contrast agent uptake times are stored from a plurality of prior contrast agent enhanced angiography imaging scans of other subjects;
   a contrast agent detection circuit which verifies a successful detection of the contrast agent in a current subject and loads the contrast agent uptake times into the parameter compilation memory;
   a reconstruction processor which reconstructs received data signals into an image representation of the current subject.

14. The diagnostic imaging apparatus as set forth in claim 13, wherein the parameter compilation memory includes a download portion by which it integrates a parameter compilation memory of at least one other diagnostic imaging apparatus into its own parameter compilation memory.

15. The diagnostic imaging apparatus as set forth in claim 13, wherein the parameter compilation memory stores and correlates the uptake times derived from diagnostic images of the other subjects and corresponding diagnoses of the other subjects, and further including:
   a means for generating contrast agent enhanced diagnostic images;
   a means for determining the contrast agent uptake times of current subjects;
   a means for comparing the current subject uptake times with the uptake times of the other subjects stored in the parameter compilation memory and retrieving a proposed diagnosis.

16. A diagnostic imaging apparatus comprising:
   a parameter compilation memory in which contrast agent uptake times and physical condition correlations are stored from a plurality of prior contrast agent enhanced angiography imaging scans of other subjects;
   a contrast agent detection circuit which verifies an actual detection of the contrast agent at an uptake time $t_D$ of an imaged patient;
   a diagnostic imaging device which collects image data of the imaged patient in a temporal window that encompasses the actual detection of the contrast agent;
   a reconstruction processor which reconstructs the collected image data into image representations of the imaged patient;
   an image analyzer that calculates an arterial arrival time $t_A$ and a venous arrival time $t_V$ from the reconstructed image representation; and,
   a means for loading the actual detection time $t_D$, the arterial arrival time $t_A$, the venous arrival time $t_V$, and correlated physical conditions of the imaged patient into the parameter compilation memory.

17. A diagnostic imaging apparatus that generates contrast agent enhanced angiographic images, the apparatus including:
   a means for generating contrast agent enhanced diagnostic images;
   a parameter memory that holds contrast agent related parameters of past diagnostic images of a plurality of patients and corresponding diagnoses;
   a means for predicting contrast agent related parameters of a present patient from the contrast agent related parameters;
   a means for comparing the present patient parameters with the parameters from the past patient diagnostic images;
   a means for analyzing the past patient parameters and the present patient parameters to offer diagnosing assistance.

18. An angiographic imaging apparatus comprising:
   a means for generating contrast agent enhanced diagnostic images of a region of interest of a patient disposed in an examination region;
   a means for monitoring and timing arrival of a bolus of injected contrast agent in the examination region;

a memory means for storing
   (1) contrast agent arrival timing for a multiplicity of prior patients and
   (2) prior patient physiological characteristics;
a means for determining a projected contrast agent arrival window from the stored contrast agent arrival times of patients with similar physiological characteristics and at least one of:

(1) blocking the image generating means from generating an image outside of the contrast agent arrival window and
(2) causing the image generating means to initiate generating a diagnostic image at the end of the projected contrast agent arrival window.

* * * * *